US00PP10720P

United States Patent [19]

Hammond

[11] Patent Number: Plant 10,720

[45] Date of Patent: Dec. 15, 1998

[54] ARGYRANTHEMUM FRUTESCENS CULTIVAR NAMED 'BLANCHE'

[76] Inventor: Frank Hammond, 100 Boundary Road, Narre Warren East, Victoria 3804, Australia

[21] Appl. No.: 846,476

[22] Filed: May 1, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

P.P. 10,298 3/1998 Cunneen ..... Plt./68.1

*Primary Examiner*—Howard J. Locker
*Assistant Examiner*—Kent L. Bell

[57] ABSTRACT

A new and distinct selection of Silver Flower which shall be referred hereinafter as *Argyranthemum frutescens* cultivar 'Blanche'. *Argyranthemum frutescens* cultivar Blanche differs distinctively from other *Argyranthemum frutescens* plants by its unique combination of a dense consistent growth habit with uniformily sized white blooms and yellow centers backed by grey green foliage.

1 Drawing Sheet

BACKGROUND OF THE INVENTION

This invention relates to a new and distinct selection of *Argyranthemum frutescens* (L.) Schutz-Bip., native to the Canary Islands and a member of the Compositae family. *Argyranthemum frutescens* cv. 'Blanche' was a chance seedling that was found among existing stock of non clonal *Argyranthemum frutescens*. I selected this seedling in January 1993. My discovery was made at 100 Boundary Road, Narre Warren East, Victoria, Australia. Selection was based on the more compact growth habit and profuse blooming. My new plant has been asexually reproduced by cuttings since the discovery in 1993 at 100 Boundary Road, Narre Warren Wast, Victoria, Australia and later at Monrovia Nursery Company, 18331 E. Foothill Boulevard, Azusa, Calif. Had this seedling not been discovered and propagated, it may have been lost to mankind. It is unlikely these particular select and favorable attributes of the plant could be conveyed to progeny through sexual reproduction in the next generation. However, through extensive propagation by rooting of the plant it has been established that the novel exceptional characteristics of this plant are stable and reliably passed on to clonal specimens through asexual reproduction.

SUMMARY OF THE INVENTION

*Argyranthemum frutescens* cv. 'Blanche' was selected for its uniform habit and grey green foliage. In comparison to another selection of mine cultivar 'Annabel' (U.S. Plant patent application Ser. No. 08/851,475 which also has white blooms with yellow centers, the two selections are easily identified. In California plants of the same age exhibit a height of 22 centimeters for cv. 'Blanche' and 52 cm for 'Annabel'. The foliage length of 'Annabel' is almost twice as long and a yellow green color whereas the shorter foliage on cultivar 'Blanche' is a more grey green. This grey green foliage color enhances the white and yellow blooms giving a rich oveall color to the plant. The diameter of the bloom is smaller on 'Blanche' than on 'Annabel', however, the bloom size is more consistent and less variable than on cultivar 'Annabel'. Cultivar 'Blanche' provides a smaller more uniform habit and bloom than has currently been available for landscape use.

This application is co-pending with those of four other Argyranthemum selections. Both 'Gretel' (U.S. Plant patent application Ser. No. 08/846,475) and 'Carmella' (U.S. Plant patent application Ser. No. 08/846,477) differ significantly In their pink ray florets. 'Primrose Petite' (U.S. Plant patent application Ser. No. 08/848,790) possesses yellow ray florets. The final selection 'Annabel' (U.S. Plant patent application Ser. No. 08/851,475) differs significantly from 'Blanche' in possessing a larger overall growth habit of twice as tall along with comparisons outlined above.

My selection *Argyranthemum frutescens* cv. 'Blanche' has tolerated a −5 degree Celsius temperature which is equivalent to a U.S.D.A. hardiness zone seven with no harm or damage. Winter protection is necessary from heavy frost.

BRIEF DESCRIPTION OF ILLUSTRATION

The accompanying photograph shows the plant in flower. The bloom color and size is very uniform and consistent with no visible fading of the white and yellow flowers as they mature.

BOTANICAL DESCRIPTION

Below is a detailed description of *Argyranthemum frutescens* cultivar 'Blanche', the color terminology is from The Royal Horticulural Colour Charts. Measurements are based on 20 random samples taken in Australia.

Botanical description:

*Overall habit.*—Perennial, subshrub.

*Overall size.*—Height — 22.0 cm (±2.0 cm). Width — 38.4 cm (±4.0 cm).

Bloom season in australia: Heaviest bloom in Spring for 10 weeks.

*Melbourne.*—6–8 months per year.

*Brisbane.*—6–8 months per year.

*Bloom lastingness.*—7 to 14 per flower.

Foliage:

*Arrangement.*—Alternate.

*Surface.*—Upper: glabrous. Lower: glabrous.

*Shape.*—Pinnatisect, primary segments 3 to 5 .

*Margins.*—Deeply to lightly parted, lobes end with mucronulate tip.

*Size.*—Length: 44.8 mm (±3.3 mm). Width: 23.9 mm (±2.1 mm).

*Color.*—Upper leaf surface: Green 137A and Yellow Green 146A (Leek Green 000858-British Horticultural Color Chart). Lower leaf surface; slightly lighter in color a Yellow Green 146A (Spinach Green 0960-British Horticultural Color Chart).

*Texture.*—Fleshy, succulent.

Inflorescences:

*Bud shape.*—Globose.

*Bud length.*—7 mm.

*Bud width.*—7 mm.

*Bud color.*—Spinach Green 0960/3 with paper Like bracts of Spanish Orange 010/1.

*Arrangement.*—Heterogamus capitulum, 1 per peduncle.

*Capitulum diameter.*—34.5 mm (±1.8 mm).

*Peduncle length.*—5.5–6.5 cm.

*Disc floret color.*—Yellow-Orange 14A and Yellow 12A. (Chinese Yellow 606-British Horticultural Color Chart).

*Disc flowerhead diameter.*—1.5 cm (±0.2 cm).

*Disc floret reproductive organs.*—Pistillate and staminate organs present.

*Ray floret number.*—Average 20–21.

*Ray floret aspect.*—Flattened at right angles to Peduncle at anthesis.

*Ray floret shape.*—Ligulate.

*Ray floret length.*—12 mm.

*Ray floret width.*—5 mm.

*Ray floret color.*—White 155D-no fading with age (No equivalent white shade in British Horticultural Color Chart) on under and upper surface.

*Ray floret shape of tip.*—Rounded, emarginate tip.

*Ray floret reproductive organs.*—Pistillate organs present.

*Frangrance.*—Light faint scent of inflorescence.

*Basal line.*—Not present.

Fruit: A 2–4 angled cypsela, 1 winged.

Disease resistance: The rust diseases of the genera Coleosporium and Cronartium are not known to occur on my selection in Australia.

I Claim:

1. A new and distinct *Argyranthemum frutescens* plant substantially as shown and described which differs distinctively from other *Argyranthemum frutescens* plants by its unique combination of a dense consistent growth habit with uniformily sized white blooms and yellow centers backed by grey green foliage.

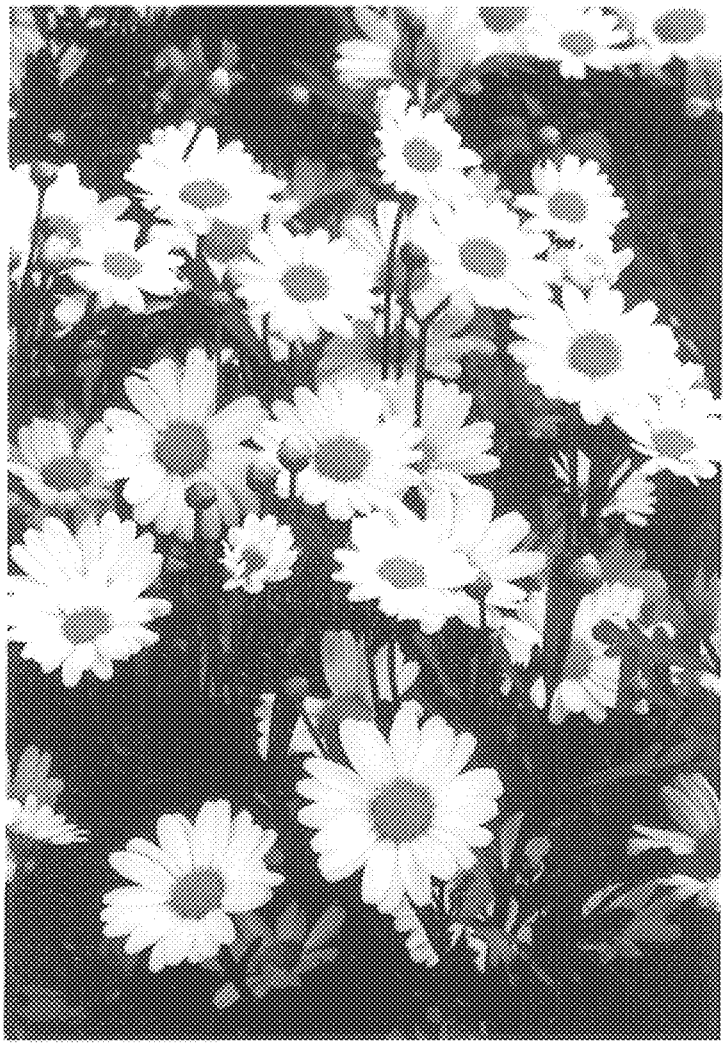

* * * * *